United States Patent [19]

Nonami et al.

[11] Patent Number: 5,125,971
[45] Date of Patent: Jun. 30, 1992

[54] LIVING HARD TISSUE REPLACEMENT, ITS PREPARATION

[75] Inventors: Tohru Nonami, Ichikawa; Nobuo Yasui, Narita, both of Japan

[73] Assignee: TDK Corporation, Tokyo, Japan

[21] Appl. No.: 545,599

[22] Filed: Jun. 29, 1990

[30] Foreign Application Priority Data

Jun. 30, 1989 [JP] Japan .................................. 1-168373
Jun. 14, 1990 [JP] Japan .................................. 2-155666

[51] Int. Cl.$^5$ .................................................. C09K 3/00
[52] U.S. Cl. .................. 106/35; 501/1; 501/123; 501/154; 433/228.1
[58] Field of Search ............... 106/35; 501/1.123, 154; 623/16; 433/228.1

[56] References Cited

U.S. PATENT DOCUMENTS 4,608,350 8/1986 Howard, Jr. .............................. 501/1
4,681,809 7/1987 Kitano .................................. 501/123
4,846,393 11/1989 Devillard .............................. 228/178

FOREIGN PATENT DOCUMENTS 0280592 8/1988 European Pat. Off.
2597745 10/1987 France.

*Primary Examiner*—Mark L. Bell
*Assistant Examiner*—Deborah Jones
*Attorney, Agent, or Firm*—Oblon, Spivak, McClelland, Maier & Neustadt

[57] ABSTRACT

A living hard tissue replacement is prepared by superplastic forming a ceramic material which contains CaO, $SiO_2$, and MgO, is substantially free of calcium phosphate, but capable of forming a calcium phosphate base compound upon contact with phosphorus-containing water. A replacement is also prepared by superplastic forming a sintered composite body comprising a calcium phosphate base ceramic matrix and an inorganic filler dispersed therein. Both the replacements are suitable as artificial dental roots and crowns.

11 Claims, 6 Drawing Sheets

LIVING HARD TISSUE REPLACEMENT, ITS PREPARATION

CROSS-REFERENCE TO RELATED APPLICATIONS

This application is related to the following co-pending applications which are assigned to a common assignee and are incorporated herein by reference:

Nonami and Yasui, U.S. Ser. No. 374,989 filed Jul. 3, 1989 for "Biomedical Material and Method for Making";

Nonami and Yasui, U.S. Ser. No. 441,775 filed Nov. 27, 1989 for "Biomedical Material and Method for Making";

Nonami, Noma, and Nakajima, U.S. Ser. No. 533,768 filed Jun. 6, 1990, for "Materials for Living Hard Tissue Replacements"; and Wakai, Kodama, Nonami, and Yasui, U.S. Ser. No. 540926, filed Jun. 20, 1990, for "Living Hard Tissue Replacement, Its Preparation, and Preparation of Composite Body."

This invention relates to living hard tissue replacements and a method for preparing the same.

BACKGROUND OF THE INVENTION

A variety of filling and repairing materials have been utilized to restore the function and configuration of a deficient part of a living body. Typical filling and repairing materials for living bodies include artificial bones and analogues such as artificial dental roots and crowns as well as artificial joints. They are generally known as living hard tissue replacements.

These living hard tissue replacements are required to be mechanically strong, tough, and stable in living bodies and should have high affinity to living bodies. Another important factor is ease of shaping because a living hard tissue replacement has to be a custom-made part conforming to an individual patient's deficient site.

The biological affinity used in this context means how a living hard tissue replacement adapts itself to and merges or assimilates with the surrounding living tissue where the replacement is embedded or implanted. Thus, a material having high biological affinity is scarcely recognized as xenobiotic by the surrounding tissue. Particularly when such material is used as an artificial bone, it can promote osteogenesis from the surrounding bone to eventually form a firm bond between itself and the bone tissue.

Among the currently available artificial bone materials, those featuring high mechanical strength and in vivo stability are metals such as titanium and zirconium, alloys containing such metals, and ceramics such as alumina, silicon nitride, and zirconia. The materials having high mechanical strength and in vivo stability, however, have low biological affinity, that is, are unlikely to assimilate with living tissue, resulting in an extended cure time and poor adherence to the living tissue. In addition, they have to be extracted and removed by surgical operations after they have performed their duties.

Typical of known materials having high biological affinity are bioglass, apatite (especially hydroxyapatite), tricalcium phosphate, and calcium phosphate crystalized glass. Apatite has the best biological affinity as understood from the fact that bone is essentially composed of apatite if organic components are excluded. These materials having high biological affinity have low mechanical strength and toughness. Since normally a pressure of about 30 kg/cm$^2$ and sometimes a maximum pressure of about 300 kg/cm$^2$ is applied to the dental root during mastication, artificial dental roots of apatite seem unreliable in durability.

We discovered that among ceramic materials which contain CaO and SiO$_2$ as essential components and optionally MgO, diopside, wollastonite and analogues, upon contact with body fluids, form a calcium phosphate base compound at the contact area so that these materials exhibit improved biological affinity, especially biological activity although they are non calcium phosphate ceramics. This is the subject matter of our preceding application, Japanese Patent Application No. 142058/1989 filed Jun. 6, 1989 (U.S. Ser. No. 07/533768 filed Jun. 6, 1990 or EPA 90110716.9 filed Jun. 6, 1990). These ceramic materials are suitable as living hard tissue replacements since they can compensate for the mechanical strength and toughness calcium phosphate base ceramic materials lack, without detracting from the biological affinity characteristic of calcium phosphate base ceramic materials.

In our preceding application, the ceramic materials are sintered at a temperature of 1,100° to 1,550° C. into a sintered body. In one preferred embodiment, the sintered body is pulverlized into a powder which is applied and joined to a substrate by spray coating, solvent welding, solution coating, or sputtering. To obtain a living hard tissue replacement having a complex profile, the sintered body has to be machined with difficulty. The preferred embodiment in which the ceramic material is bonded to a substrate has some likelihood that exfoliation can occur at the interface during repetitive use, indicating that the bonding force is less satisfactory. There are additional problems that the coating thickness is less uniform and shaping to a complex configuration is difficult.

It was believed in the prior art that ceramics can be shaped only by sintering. However, like metals, attempts have been made to subject ceramics to plastic forming, for example, by forging, extruding and rolling. For the plastic forming of ceramics, it is necessary to heat the material to a temperature higher than its melting point by about 60% or more, and the heating temperature can reach 2,000° C. for a certain material. Nevertheless, those ceramic materials having superplasticity show extremely greater ductility, sometimes 10 times greater ductility, under low stresses at a temperature substantially lower, e.g., by 500° C., than the sintering or forging temperature as described in the literature, for example, Journal of the JSTP, 29, 326 (March 1988); Ceramics, 24, 2 (1989); and Tetsu to Hagane (Iron and Steel), 75, 3 (1989). Typical prior art ceramic materials known to show superplastic nature are Y-TZP (yttria-stabilized tetragonal ZrO$_2$ polycrystals) and ZrO$_2$-Al$_2$O$_3$ systems. To take advantage of plastic deformation, extrusion molding and thin plate molding have been attempted on them. Attempts have also been made to diffusion bond two pieces of the same material by superplastic forming.

We have discovered that calcium phosphate base ceramic materials including apatite and tricalcium phosphate show superplastic nature. This is the subject matter of our application, Japanese Patent Application No. 155758/1989 filed Jun. 20, 1989 (U.S. Ser. No. 540926 filed Jun. 20, 1990.

However, no study has been made on the superplasticity of diopside. We have discovered that a superplastic phenomenon also develops with non-calcium phosphate base ceramic materials such as diopside.

We proposed in Japanese Patent Application No. 164959/1988 filed Jul. 4, 1988 (U.S. Ser. No. 374,989 filed Jul. 3, 1989 or EPA 89112220.2 filed Jul. 4, 1989), a sintered composite body having increased mechanical strength comprising a biologically active ceramic matrix such as apatite and inorganic whiskers dispersed therein. We have also discovered that this material can be subject to superplastic forming.

SUMMARY OF THE INVENTION

For the purpose of improving the generally low mechanical strength and toughness of biologically active ceramic materials, especially living hard tissue replacements of calcium phosphate base ceramic materials, we have selected as the first candidate a ceramic material which contains CaO and $SiO_2$ as essential components and can form a calcium phosphate compound upon contact with a phosphorus-containing aqueous fluid in a living body. The second candidate we have selected is a sintered composite body comprising a calcium phosphate base ceramic matrix and an inorganic filler dispersed therein.

Therefore, a primary object of the present invention is to provide a novel and improved living hard tissue replacement which can be readily formed to the desired shape, surface nature, and dimensions in conformity to an individual patient. Another object is to provide a method for preparing such a living hard tissue replacement.

In the first form, the present invention provides a living hard tissue replacement prepared by the superplastic forming of a ceramic material which contains CaO and $SiO_2$ as essential components, is substantially free from calcium phosphate, but capable of forming a calcium phosphate base compound upon contact with a phosphorus containing aqueous solution. The invention also provides a method for preparing a living hard tissue replacement comprising the step of superplastic forming the ceramic material defined above. Most often, the ceramic material further contains MgO and the ceramic material belongs to the diopside, wollastonite, akermanite, monticellite, alite, or belite field.

In the second form, the present invention provides a living hard tissue replacement prepared by the superplastic forming of a sintered composite body comprising a calcium phosphate base ceramic matrix and an inorganic filler dispersed in the matrix. The invention also provides a method for preparing a living hard tissue replacement comprising the step of superplastic forming the sintered composite body defined above.

The living hard tissue replacement is most often used as an artificial dental root or crown.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE INVENTION

The first form of the invention uses a non-calcium phosphate ceramic material which contains CaO and $SiO_2$ as essential components and can form a calcium phosphate base compound upon contact with a phosphorus-containing aqueous solution. It has never been reported that ceramic materials containing CaO and $SiO_2$ as essential components have superplastic nature. The ceramic materials containing CaO and $SiO_2$ as essential components and substantially free of calcium phosphate preferably contain CaO and $SiO_2$ in a weight ratio of from 1:4 to 6:1, more preferably from 1:3 to 2:1. Strength and biological affinity become less desirable outside the range. The ceramic materials may further contain MgO in an amount of up to 35% by weight based on the total weight of the material. Inclusion of MgO has the advantages of lower sintering temperatures and improved adhesion to bones.

The ceramic materials containing calcium oxide and silicon dioxide as essential components are generally composed of 10 to 90%, especially 7 to 77% by weight of CaO, 10 to 80%, especially 23 to 70% by weight of $SiO_2$, and 0 to 35% by weight of MgO based on the total weight. The preferred composition is 7 to 65% by weight of CaO, 40 to 70% by weight of $SiO_2$, and 0 to 35% by weight of MgO. Better results are obtained when the ceramic composition is composed of 7 to 40% by weight of CaO, 45 to 70% by weight of $SiO_2$, and 8 to 35% by weight of MgO.

The ceramic materials used in the present invention are characterized in that upon contact with an aqueous solution containing phosphorus, for instance, spurious and true body fluids, they form calcium phosphate base compounds, typically hydroxyapatite on their surfaces of contact. This characteristic feature ensures that when they are implanted in a living system, an amorphous calcium phosphate base compound with satisfactory biological affinity uniformly and rapidly precipitates on their surfaces of contact with living bones, so promoting the formation of neoblastic bones. In addition, the thus formed junctions with living bones are very firm since the junctions have a graded concentration of composition with crystallographical continuity established between the implants and the living bones.

The ceramic materials used herein generally have a composition belonging to the fields of diopside $CaO.2SiO_2.MgO$, wollastonite $CaO.SiO_2$, alite $3CaO.SiO_2$, belite $2CaO.SiO_2$, akermanite $2CaO.2SiO_2.MgO$, montecellite $CaO.SiO_2.MgO$, forsterite, proteoenstatite, tridymite and so on. Among others, preference is given to diopside, wollastonite, alite, belite, akermanite, and monticellite. The most preference is given to ceramic materials predominantly comprising diopside and wollastonite compositions and having relatively low sintering temperatures of 1,200° to 1,350° C. because of their high biological affinity. In particular, ceramic materials containing diopside components, especially those having a composition belonging to the diopside field have high flexural strength and biological affinity.

Figure 7:
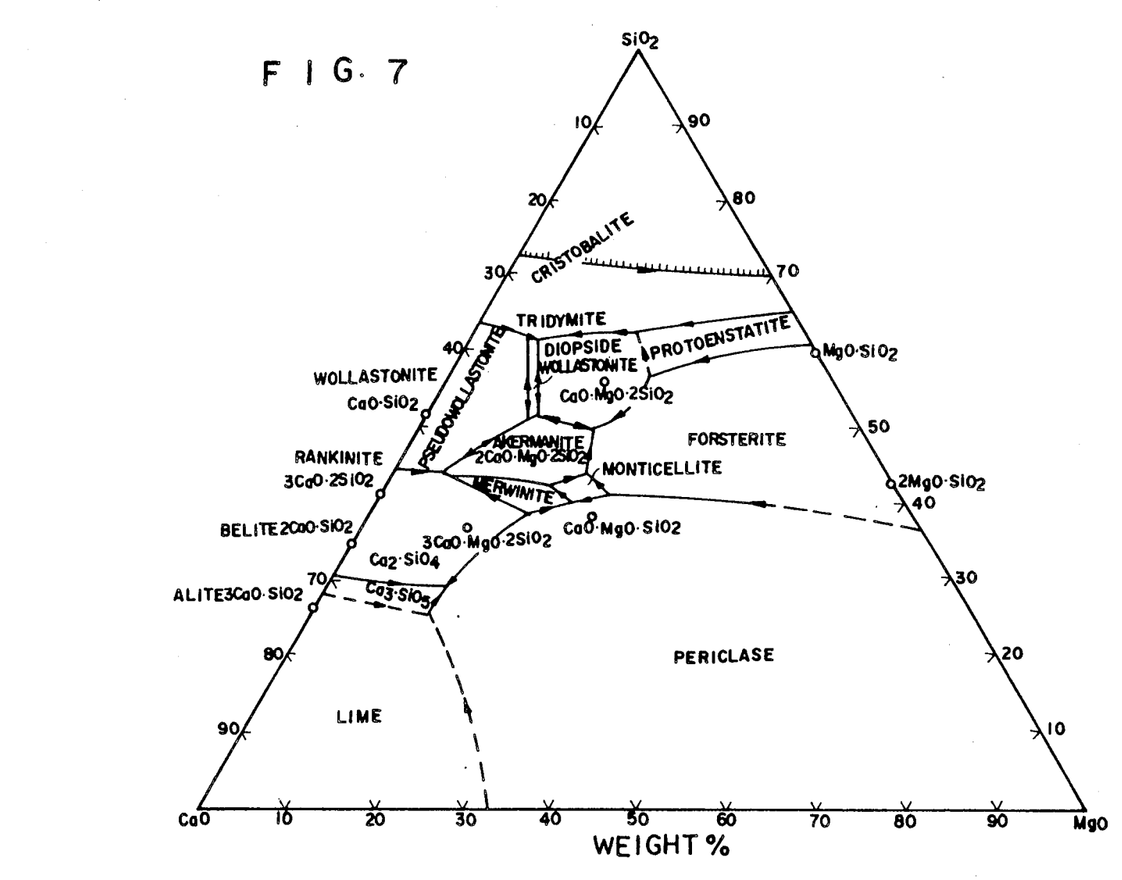
FIG. 7 is a phase diagram of a $CaO-MgO-SiO_2$ ceramic system.

FIG. 7 is a phase diagram of a $CaO-MgO-SiO_2$ system in which the diopside, wollastonite, and other fields are delimited. Preferably, the phases of diopside and wollastonite, particularly that of diopside, occupy at least 40% by volume, especially at least 50% by volume, more especially 70 to 100% by volume of ceramic materials. The quantity of such phases contained in ceramics may be determined by X-ray powder diffraction methods.

The ceramic materials used herein are generally prepared by mixing together calcium oxide, silicon oxide, and optionally magnesium oxide in a predetermined proportion, calcining or pre sintering the mixture, pulverizing the calcined product, and then sintering the powder again. In place of the oxides, use may be made of substances capable of producing such oxides under sintering conditions such as carbonates, bicarbonates, and hydroxides of calcium and magnesium and silicic acid. Such stock materials may be used not only in powder or granular form, but also in slurry or solution form. Instead of the stock materials corresponding to the respective components, use may also be made of preformed diopside $CaO.2SiO_2.MgO$ or compositions belonging to the diopside field after pulverizing them into powder. Alternatively, use may be made of mixtures of diopside with other analogous substances such as wollastonite, forsterite, akermanite, proteoenstatite, tridymite, and belite. Such analogous substances are obtained as by-products during preparation of ceramic materials whose composition belongs to the diopside field if any one of calcium, magnesium and silicon oxide feed stocks is used in excess.

It is acceptable to blend additives to the ceramic materials such that there may be present $P_2O_5$, $TiO_2$, $Al_2O_3$, $Na_2O$, $K_2O$, and $B_2O_3$ in a total amount of up to 5% by weight.

The ceramic materials are prepared from such stock materials by pulverlizing the stock materials into powders and mixing them together in a mixing machine such as a ball mill, vibratory mill, automatic mortar, mixer, juicer, sand mill and whipping unit. The mixture is then dried at 50° to 300° C. for 10 minutes to 100 hours and calcined or pre-sintered at 500° to 1,600° C., preferably 800° to 1,600° C. for 10 minutes to 200 hours. The calcined product is pulverized and molded into a compact of desired shape by pressing, slip casting, etc., while a binder such as polyvinyl alcohol is added if required. The compact is dried and finally sintered at a temperature of from 800° to 1,700° C., preferably from 900° to 1,600° C. In this procedure, the powders of stock materials should have a particle size corresponding to a BET value of usually at least 0.5 $m^2/g$, preferably at least 1 $m^2/g$, more preferably at least 3 $m^2/g$. The molding pressure ranges from 1 to 3,000 $kg/cm^2$. The sintering time usually ranges from 10 minutes to 20 hours. Sintering is usually carried out under atmospheric pressure, but under an increased pressure in the range of from 10 to 3,000 $kg/cm^2$ if required.

The ceramic materials resulting from sintering preferably have an average grain size of up to 10 $\mu m$, more preferably from 0.005 to 1 $\mu m$ and a relative density of at least about 70%, more preferably at least 90%, most preferably at least 99.5%. Then the ceramic materials develop a superplastic phenomenon at a temperature in the range of from 800° to 1,600° C. It is to be noted that the average grain size may be measured by means of a scanning electron microscope (SEM) by determining an average grain area, and determining the average diameter of a phantom circle having the average grain area. The average diameter is the average grain size.

During sintering, concurrent hot pressing (HP) or hot isostatic pressing (HIP) is preferably carried out for densification purposes. The sintering atmosphere may be an inert gas, air, hydrogen or vacuum. The compact may be calcined or pre-sintered at at temperature of 50° to 300° C. for about 3 minutes to about 30 hours before it is sintered.

Whiskers may be contained in the sintered body for the purpose of increasing mechanical strength insofar as superplasticity is not detrimentally affected.

The sintered body may take the form of a porous body having independent and interconnected cells. Since the ceramic materials of the invention have higher strength than the conventional calcium phosphate base materials, such a porous body can be produced so as to have any desired pore diameter and porosity while maintaining high biological affinity. The porous body generally has a pore diameter of 5 to 2,000 $\mu m$, preferably 10 to 1,000 $\mu m$ and a porosity of 10 to 80%, preferably 20 to 70%, more preferably 25 to 60%.

The porous body may be prepared according to well-known methods for the manufacture of porous ceramics, by mixing the stock material mixture with a pyrolytic substance or organic fibers, followed by sintering. The thus sintered porous body usually has a compression strength of at least 7 MPa, preferably at least 10 MPa, more preferably at least 15 MPa.

The ceramic materials thus obtained may be used either as blocks of the required shape or in the form of granules suitable for filling in bone defects.

The second form of the present invention employs a sintered composite body comprising a calcium phosphate base ceramic matrix and an inorganic filler dispersed in the matrix.

The materials which constitute the ceramic matrix of the sintered composite body are calcium phosphate materials having high biological activity and suitable as biomedical implant materials.

The calcium phosphate materials used as sintering stock material in the practice of the present invention include a variety of calcium phosphate compounds, for example, tri-calcium phosphate $Ca_3(PO_4)_2$, and apatite series calcium phosphates $Ca_{10}(PO_4)_6X_2$ wherein X is OH, halogen (e.g., fluoro and chloro), $CO_3$ or the like, such as hydroxyapatite, fluoroapatite, chloroapatite, and carbonated apatite. They may be used alone or in admixture of two or more.

Preferred calcium phosphates are of the apatite series, especially hydroxyapatite and fluoroapatite. These apatites may be either synthetic apatites prepared by dry and wet processes or biotic apatites collected from bones and teeth of various vertebrate animals. A typical dry synthetic process is by reacting calcium phosphate with excess CaO in a steam stream at a high temperature of 900° to 1,300° C.

The preferred calcium phosphate materials used herein are apatites, especially hydroxyapatites and fluoroapatites, having an atomic calcium to phosphorus (Ca/P) ratio of from 160/100 to 175/100, especially from 165/100 to 175/100. Hydroxyapatites are most preferred.

The calcium phosphate materials forming the matrix are used in the form of powder having a particle size of 0.05 to 1,000 $\mu m$ or granules having a particle size of 0.1 to 3 mm. The powder or granules preferably have a surface area of about 0.01 to 300 m$^2$/g in BET value.

In the practice of the invention, the above-mentioned calcium phosphate materials should be eventually sintered into calcium phosphate base ceramic matrixes having a grain size of 0.05 to 30 μm, preferably 0.05 to 10 μm, more preferably 0.05 to 10 μm, most preferably 0.05 to 2 μm. A grain size smaller than the lower limit is difficult to achieve whereas a grain size larger than the upper limit results in a reduced strength and is less susceptible to superplastic forming.

The inorganic fillers are not particularly limited although whiskers are preferred for toughness. The inorganic fillers used herein include oxide fillers, for example, those containing at least one of silicon oxide, calcium oxide, aluminum oxide, magnesium oxide, and zirconium oxide, more illustratively alumina, zirconia, calcium silicate, aluminum silicate, aluminum silicate calcium, calcium silicate magnesium, calcium aluminate, and magnesium silicate; silicon nitride fillers; carbide fillers, for example, silicon carbide and boron carbide; carbon fillers; and metal fillers, for example, titanium and titanium alloy.

For biological compatibility and affinity, preferred fillers are alumina, zirconia, aluminum silicate calcium systems such as anorthite CaO.2SiO$_2$.Al$_2$O$_3$, calcium silicate magnesium systems such as diopside CaO.2SiO$_2$.MgO, and calcium silicate systems such as wollastonite CaO.SiO$_2$. Among others, oxide fillers containing at least one of silicon oxide (silica), calcium oxide (calcia), aluminum oxide (alumina), and magnesium oxide (magnesia), more preferably those containing at least two of silica, calcia, and alumina, especially those containing silica, calcia, and alumina and/or magnesia are preferred for biological activity and affinity. The most preferred fillers are those having a composition corresponding to the anorthite, diopside or wollastonite field and containing, in % by weight, 10 to 80% of SiO$_2$, 10 to 90% of CaO, 0 to 35% of MgO, and 0 to 35% of Al$_2$O$_3$. It will be appreciated that the fillers or whiskers may have a composition deviating more or less from the stoichiometry shown above.

The inorganic fillers or whiskers are generally used in amounts of about 0.5 to about 95% by weight, preferably about 5 to about 70% by weight, more preferably about 10 to about 60% by weight, further preferably about 10 to about 50% by weight, most preferably about 10 to about 40% by weight of the composite ceramic material. If inorganic fillers are used in more amounts beyond the range, the desirable properties of the matrix or calcium phosphate, for example, the biological affinity of apatite as artificial bone are reduced or lost. Materials containing less amounts of inorganic fillers will result in sintered bodies having low mechanical strength (e.g., compression strength) and toughness with a loss of workability and productivity.

It will be understood that when pre-formed fillers or whiskers are used, the fillers or whiskers in the resulting sintered body have approximately the same dimensions as the original.

Filler or whisker-forming materials, that is, materials which can convert into fillers or whiskers under sintering conditions may also be used, for example, silica, calcium oxide, magnesium oxide, and alumina, as well as those which can convert into these compounds upon sintering, such as corresponding carbonates, bicarbonates, and hydroxides. These materials may be used in the form of powder, granules, slurry, and aqueous solution.

The materials in the form of powder or granules preferably have a BET value of about 0.01 to about 300 m$^2$/g.

These filler-forming materials may be blended in such a proportion corresponding to the composition of the desired fillers. Useful are blends comprising a silica source in an amount of 0.05 to 800 parts by weight of SiO$_2$, a calcium oxide source in an amount of 0.05 to 600 parts by weight of CaO, and an alumina source in an amount of 0.05 to 600 parts by weight of Al$_2$O$_3$ and/or a magnesia source in an amount of 0.05 to 600 parts by weight of MgO, all parts being per 100 parts by weight of the matrix (calcium phosphate) material. In these blends, the sources are preferably blended in such proportions that 0.5 to 20 mol of silica, 0.1 to 20 mol of alumina and 0.1 to 20 mol of magnesia are present per mol of calcium oxide.

In addition, one or more of zirconia, strontium oxide, and barium oxide sources may be used in sufficient amounts to provide up to 20% by weight of ZrO$_2$, SrO, and BaO.

When it is desired to grow diopside fillers or whiskers, for example, the source may be blended in such proportions that 0.15 to 14 mol, preferably 0.5 to 5 mol, more preferably 0.8 to 2.5 mol, most preferably 0.8 to 1.2 mol of magnesium oxide and 0.5 to 10 mol, preferably 2 to 5 mol, more preferably 2 to 3 mol, most preferably 2 to 2.5 mol of silica are present per mol of calcium oxide. When it is desired to grow anorthite fillers or whiskers, for example, the sources may be blended in such proportions that 0.1 to 20 mol, preferably 0.2 to 1.5 mol, more preferably 0.8 to 1.2 mol of alumina and 1 to 10 mol, preferably 2 to 5 mol, more preferably 2 to 3 mol, most preferably 2 to 2.5 mol of silica are present per mol of calcium oxide.

These sources may be added individually to the calcium phosphate component. Instead of individual addition, it is also possible to add a single component capable of forming fillers or whiskers, for example, a diopside component corresponding to composition CaO.2SiO$_2$.MgO and an anorthite component corresponding to composition CaO.2SiO$_2$.Al$_2$O$_3$. These components may also be used in powder or granule form like the calcium phosphate component. The whisker-forming components in powder form preferably has a BET value of about 0.01 to about 300 m$^2$/g.

A mixture of two types of stock materials, a calcium phosphate-forming component and a filler or filler-forming component as described above, is sintered into a sintered composite body consisting essentially of 5 to 95% by weight of crystalline calcium phosphate or matrix and 95 to 5% by weight of the filler, typically diopside or anorthite. The presence of matrix and filler by-products created upon sintering is permitted as long as the desired effect is not impaired. In the examples mentioned above, permissible is inclusion of such by-products as α-tricalcium phosphate and other oxides such as forsterite and wollastonite in the case of diopside filler and akermanite and mullite in the case of anorthite filler. The by-products are usually copresent in the matrix.

In the case of forming whiskers upon sintering, the whisker-forming material preferably has a sintering temperature higher by 50° to 400° C. than the sintering temperature of the calcium phosphate material. Source materials as described above may be readily blended so as to give such a sintering temperature. The sintering temperature of a material can be readily determined by measuring an increase of shrinkage factor using a thermo-dilatometer.

In the sintered composite body, the calcium phosphate forming the matrix is present as crystals and the fillers or whiskers are dispersed in the matrix.

The fillers or whiskers each have a length and a diameter. The whisker length is in the range of from 0.05 to 30 μm, preferably from 0.5 to 15 μm, more preferably from 0.05 to 5 μm, further preferably from 0.05 to 3 μm, most preferably from 0.05 to 2 μm. The aspect ratio defined as length divided by diameter is in the range of from 1/1 to 100/1, preferably from 1.2/1 to 100/1, more preferably from 1.5/1 to 100/1, further from 2/1 to 20/1, most preferably from 3/1 to 15/1. Shorter fillers or whiskers outside the length range are less effective whereas longer fillers or whiskers tend to induce strains. Fillers having an aspect ratio of less than 1 are less effective whereas fillers having an aspect ratio of more than 100 tend to induce strains.

The ratio of matrix grain size to filler length is in the range of from 10/1 to 1/10, preferably from 14/10 to 2/10, more preferably from 1/1 to 2/10. If the ratio is smaller than 1/10, strains are induced upon sintering, losing strength. If the ratio is larger than 10/1, the whiskers do not fully exert their function of increasing strength.

The fillers or whiskers occupy 0.5 to 95% by area, preferably 5 to 75% by area, more preferably 10 to 60% by area, further preferably 10 to 50% by area, most preferably 10 to 40% by area of a cross section of the sintered body. Outside the range, sintered bodies having less amounts of whiskers are less tough whereas sintered bodies having excess amounts of whiskers are low in biological affinity and less superplastic. The percent area that fillers or whiskers occupy in a cross section of the sintered body can be determined using a photomicrograph. More particularly, a sintered body sample is sectioned. The section is mirror polished, and then chemically etched with aqueous 1–5% HCl or thermally etched at a temperature of higher than 800° C., but lower than the whisker forming temperature. The section is then observed under a scanning electron microscope. The photomicrograph is then transferred to a section paper, from which the percent area of whiskers is calculated by counting the corresponding sections. The procedure may be repeated five times, for example, to determine the average percent area of whiskers.

The preparation of the sintered composite material of the present invention will be described in detail. The starting material is a calcium phosphate material powder or similar ceramic powder. A predetermined amount of whiskers or whisker-forming materials in powder form is added to the powder calcium phosphate material along with a dispersant. The whisker-forming materials are materials that can transform into whiskers under sintering conditions, for example, silica, calcium oxide, magnesium oxide, and alumina, and may be added separately or as a premix. Use of sources which produce materials that can together form whiskers under sintering conditions is also contemplated. Materials having whisker compositions such as the anorthite and diopside compositions are also useful.

The dispersant assists in uniformly dispersing whiskers or whisker-forming materials in powder calcium phosphate material. Examples of the dispersant include anionic surface-active agents such as carboxylate salts and sulfonate salts.

The thus prepared powder mixture is shaped into a desired configuration by a conventional method such as press molding and slip casting, dried, and then sintered in air at a temperature of 800° to 1600° C. Shaping is generally carried out under a pressure of 1 to 10,000 kg/cm$^2$.

Sintering is preferably effected at a temperature of 800° to 1500° C. particularly when it is desired to form anorthite whiskers in the calcium phosphate matrix. Sintering is preferably effected at a temperature of 900° to 1500° C. particularly when it is desired to form diopside whiskers in the calcium phosphate matrix. When pre-formed whiskers are used, sintering may be effected at a temperature of 800° to 1600° C. The sintering time generally ranges from about 5 minutes to about 15 hours in any cases.

At the same time as sintering, hot pressing or hot isostatic pressing may be performed under a pressure of about 50 to about 5,000 atm. Calcination or pre-sintering may be effected before sintering.

Sintering creates crystalline calcium phosphate matrix or crystalline calcium phosphate matrix and whiskers (or fillers) at the same time when the whisker-forming material is used. There is obtained a sintered composite body in which whiskers (or fillers) are dispersed in the crystalline calcium phosphate matrix, both the matrix and whiskers (or fillers) meeting the dimensional requirements.

As compared with the addition of pre-formed fillers or whiskers, it is advantageous to form fillers or whiskers simultaneous with crystalline calcium phosphate as the matrix because the resulting sintered body has improved toughness and strength due to the increased bond between the fillers or whiskers and the matrix.

When diopside whiskers free of alumina are formed, the material mixture can be sintered at a temperature in a wide range of 900° to 1500° C. without the risk of conversion of hydroxyapatite into tricalcium phosphate or $\beta$-tricalcium phosphate into $\alpha$-calcium phosphate catalyzed by alumina. Formation of anorthite whiskers also avoids such a risk because they can be formed at temperatures of lower than 1,300° C.

When the sintering temperature is set to lower than 1,300° C. in the above-defined range, a sintered body having good biological affinity and mechanical strength and toughness can be obtained even from hydroxyapatite prepared by a wet process without causing abnormal grains to grow.

The formation of fillers or whiskers during sintering is described in further detail. When the whisker-forming material or mixture used has a sintering temperature higher by 50° to 400° C. than the sintering temperature of the calcium phosphate material as previously described, the calcium phosphate is sintered in an earlier stage where the whisker component has not been activated. Consequently, the whisker component is unlikely to diffuse into the matrix in this stage. If diffusion occurs in this stage, then the respective components would change their composition with a possibility that little whiskers would form or glass would form. Such a risk is avoided by controlled diffusion of the whisker component in the early stage. Whiskers start precipitating in a later stage when calcium phosphate has been sintered to a certain extent. A practically satisfactory density is achieved without any problems that whiskers having the matrix component included therein can precipitate and that no sufficient density is available because the matrix has not been fully sintered when formation of whiskers is complete. In addition, there are little possibilities that the matrix is sintered too earlier than necessary, and premature sintering of the matrix prevents whiskers from precipitating or causes precipitating whiskers to be largely stressed.

Better results are obtained when an intermediate layer is present between grains of the crystalline calcium phosphate matrix and inorganic fillers or whiskers. The intermediate layer extends partially or entirely along the boundary therebetween. The intermediate layer contains at least one of the elements in either one or both of the whiskers and the matrix. Since some elements like calcium are common to both the whiskers and the matrix, the intermediate layer preferably contains the common element or elements. The intermediate layer has a continuous or stepwise gradient of concentration between the whiskers and the matrix grains. More illustratively, for one element contained in the whisker, the intermediate layer contains the element in a high concentration adjacent the whisker and gradually reduces its concentration toward the interface with the matrix. The intermediate layer is preferably of vitreous phase or contains a vitreous phase.

The intermediate layer generally has a thickness of up to 3 μm, preferably from 0.005 to 3 μm, more preferably from 0.005 to 1.5 μm, further preferably from 0.01 to 1.0 μm, most preferably from 0.01 to 0.2 μm.

The intermediate layer may be formed by slowly cooling down the sintered body from the sintering temperature over an extended time. Cooling is preferably performed at a slow constant rate of 0.2° to 30° C./min., more preferably 0.5° to 10° C./min.

Provision of an intermediate layer between whiskers and grains prevents direct reaction between whiskers and grains so that the whiskers are no longer changed maintaining sufficient strength, improves the bond between whiskers and grains also contributing to strength, and enables easy control of the interface between whiskers and grains. As a result, the sintered body is reinforced more densely, further improving mechanical strengths such as flexural strength and toughness. The intermediate layer containing a vitreous phase improves the ability of superplastic forming.

Orientation of whiskers in the matrix is possible and desirable, because strength is further improved. Preferably, the whiskers are present in the matrix at a degree of orientation of at least 60%, more preferably at least 75%, most preferably at least 85%.

Whiskers may be oriented by adding a binder to a blend of a calcium phosphate material and whiskers and kneading the mixture. The binder used herein may be selected from those commonly used for biomedical materials, for example, rubber or thermoplastic resins. The binder may be added to the blend in amounts commonly used for biomedical materials, generally in amounts of 10 to 50%, preferably 20 to 45% by weight of the blend. Less amounts of binder are ineffective in helping orientation whereas larger amounts of binder would result in porous sintered bodies which are low in biological affinity and density.

Next, it is necessary to process the mixture so as to have a controlled degree of orientation of whiskers of 60% or higher. In practice, the mixture is repeatedly rolled to control the degree of orientation. The rolling process renders whiskers anisotropic. Sufficient orientation may be accomplished by repeating the rolling step several times, for example, 3 to 10 times. The rolling process includes rolling techniques such as calendering, pressing techniques and extrusion techniques. Rolling techniques are preferred. The pressure under which the mixture is rolled is generally in the range of from 20 to 300 kg/cm$^2$, preferably from 50 to 150 kg/cm$^2$. Lower rolling pressures would be ineffective to provide sufficient strength whereas higher rolling pressures give no further benefits.

The mixture is thus rolled into a plate or sheet material, which is sintered into a sintered body with or without post-processing like hot pressing before sintering.

According to the present invention, the calcium oxide and silicon oxide-containing, non-calcium phosphate ceramic material in the first form and the calcium phosphate ceramic matrix/inorganic filler composite material in the second form, both sintered, are processed by superplastic forming. For brevity's sake, both the materials are often referred to as sintered ceramic materials hereinafter.

The forming temperature ranges from 500° C. to a temperature lower than the sintering temperature, preferably lower by 50° C. More illustratively, the temperature ranges from 600° to 1,600° C., often from 600° to 1,300° C., most often from 800° to 1,200° C.

The superplastic forming uses a mold with a cavity having the shape and dimensions corresponding to the intended living hard tissue replacement or implant and is performed by subjecting the sintered ceramic material to extrusion shaping or embossing. During the process, both the sintered ceramic material and the mold should be heated to a temperature at which the sintered material exhibits superplasticity. The sintered ceramic material subject to superplastic forming is preferably in the form of thin plates or sheets, granules, and powder particles. Superplastic forming causes thin sheets or granules to fuse together to form a continuous crystalline structure at their interface, resulting in a very firm junction.

The compression rate, compression force, and deformation during superplastic forming vary with a particular technique employed. Preferred forming parameters include a compression rate of 0.01 to 50 mm/min., a compression force of 1 to 2,000 MPa, more preferably 1 to 500 MPa, especially 1 to 100 MPa, and a deformation of about 0.1 to about 1.5 in true strain.

In the case of embossing, the sintered ceramic material which has been shaped to approximately the desired configuration, for example, the dental crown shape may be used. In this case, only a minimal deformation is to be achieved by superplastic forming or embossing, with the benefit of ease of forming. The superplastic forming may also be carried out by rolling, drawing, tubing, bending, shearing, deep drawing, and other pressing techniques as well as a hot pressing technique using a mold or a hot isostatic pressing (HIP) technique. Further, the superplastic forming may be repeated any times if desired.

In general, the thus formed ceramic material has experienced a change in grain size as low as 100% or less. It is sometimes observed that the grains have undergone slippage along the grain boundary, deformation, and orientation.

In one preferred embodiment of the present invention, a sintered ceramic material as previously described and a material of the same or different type are joined together by superplastic forming. More particularly, the two materials are placed in pressure contact to provide a diffusion or solid phase bond.

Pressure contact may be achieved between a sintered ceramic material and a substrate of a different material by pressing the stacked materials in close contact using a press or punch or by extruding or reverse extruding the sintered ceramic material through a die using a punch formed of the substrate material. Pressure contact may also be accomplished by rolling and drawing combined with extrusion. The superplastic forming may be repeated any times if desired.

The superplastic forming joins and shapes the sintered ceramic material and the heterogeneous material together into an integral body having a bond strength as high as 30 to 1,000 MPa, especially 100 to 1,000 MPa although the bond strength depends on the type of the heterogeneous material.

The material of different type to be joined is not particularly limited. It may be selected from various ceramic materials, various metals, various glasses, composites thereof, and other suitable materials. The material to be joined may or may not exhibit plastic deformation during pressure joining. Also, it may or may not exhibit superplastic deformation. If the material to be joined has superplastic nature, then it is possible to join three or more materials together at the same time. Most often, the material to be joined has high mechanical strength and functions as a substrate or support.

In the preferred embodiment wherein the sintered ceramic material covers a substrate of different material, two materials are held in close contact at a predetermined temperature and pressure by hot isostatic pressing (HIP), thereby achieving a diffusion or solid phase bond therebetween. The sintered ceramic material as the cover layer undergoes superplastic deformation during the HIP process.

For the HIP process, the temperature generally ranges from 500° C. to lower than the sintering temperature, usually from 500° C. to 1,600° C. The compression force generally ranges from 1 to 2,000 MPa, usually from 1 to 500 MPa. The heating/pressing time may vary over a wide range of from about 6 seconds to 25 hours. The deformation ranges from about 0.1 to about 1.5 in true strain.

Figure 1:
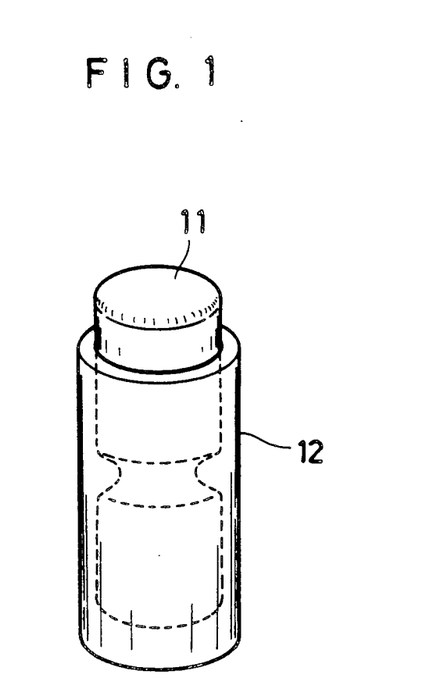
FIGS. 1 to 3 are perspective views illustrating steps of the method for preparing an integrated body as a living hard tissue replacement according to the invention.
Figure 2:
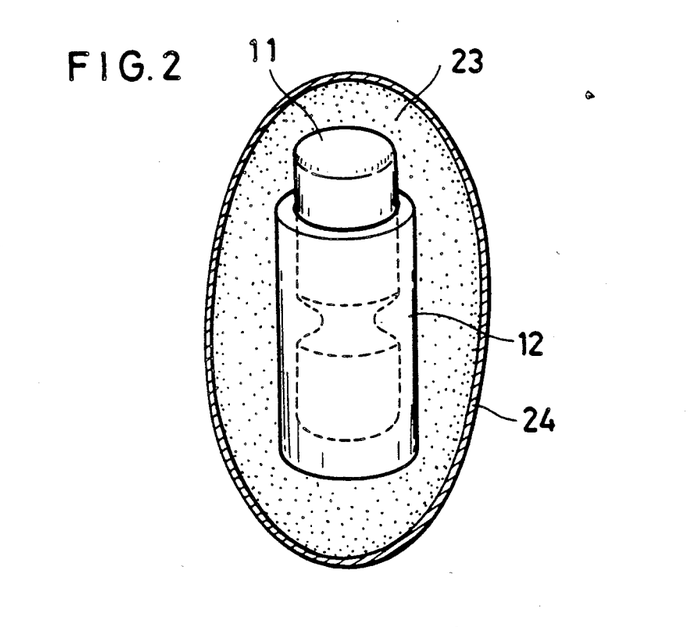
Figure 3:
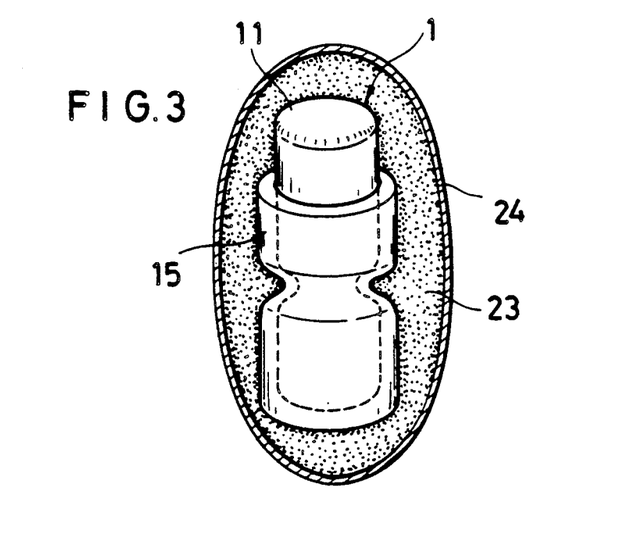

Referring to FIGS. 1 to 3, an assembly of a substrate and a cover is shown in perspective views to illustrate the method for preparing an integral body using the HIP process. The elements involved in this method are a substrate 11, a cover 12 formed of superplastic ceramic material, a surrounding/pressurizing medium 23 in the form of ceramic powder, and an enclosure 24 in the form of a glass envelope for enclosing the foregoing three elements in a stationary manner.

The substrate 11 is preferably formed of a material which can withstand repetitive stresses and has a flexural strength of 200 MPa or higher, sometimes as high as 1500 MPa and a high melting point of 700° C. or higher. Also preferably, the substrate material undergoes little deformation, say, a deformation of less than 10%, during superplastic HIP joining. Preferred examples of the substrate material include metals and ceramics, which should be safe to living bodies in the case of living hard tissue replacements.

The substrate-forming metals include elemental metals such as Ti, W, Mo, Au, and Pt and alloys such as Ni-Cr, Ni-Ti, Fe-Cr-Al, Ti-Zr, Fe-Ni-Cr, Ti-Al-V, Co-Cr, Co-Cr-Mo, Ti-Mo, and stainless steel. The metal substrate is preferably pretreated on their surface. For example, the substrate surface is roughened by blasting with #20 to #400 steel shots or etching. Similar results are obtained when a metal of the same type as the substrate is sprayed to the substrate surface by plasma or gas spraying techniques. The rough surface of the substrate resulting from any of the foregoing treatments may be further treated with a corrosive inorganic or organic acid such as hydrochloric acid, sulfuric acid, nitric acid and oxalic acid by coating or immersion and then heat treated at a temperature of 300° to 1,000° C. for one to two hours, forming an oxide on the rough surface of the metal substrate. Surface roughening optionally followed by oxide formation has the advantage that a closer contact and hence, a higher bonding force is established between the substrate and the cover because the substrate and the cover are microscopically interdigitated at their interface during joining by HIP.

The ceramics useful as the substrate 11 include high strength ceramics such as zirconia, SiC, SiN, BN, and $Al_2O_3$.

The cover 12 is of a superplastic ceramic material which is selected from biologically active ceramic materials including calcium oxide and silicon oxide-containing, non-calcium phosphate ceramic materials and calcium phosphate/filler composite materials as previously described. More particularly, the cover 12 is formed from a sintered ceramic material having a predetermined grain size. The configuration and dimensions of the cover 12 may be determined in accordance with the configuration and dimensions of the substrate 11. The sintered ceramic material of which the cover 12 is made may have a grain size one to ten times the desired grain size in the final product. It is desired that the difference in thermal expansion coefficient between the substrate 11 and the cover 12 be within 50%, preferably within 40%, more preferably within 10%.

The ceramic powder used as the surrounding/pressurizing medium 23 includes zirconia, alumina, BN, SiC, SiN, WC, and partially stabilized zirconia although high temperature ceramics which do not melt at the superplastic forming temperature involved in the HIP process, especially at 700° C. or higher temperatures are preferred. A proper choice should be made of the particle size of the ceramic powder 23 since the cover 12 joined to the substrate by superplastic forming can have a surface roughness corresponding to the selected particle size of the surrounding powder. Therefore, the ceramic powder may have a particle size of about 10 to about 500 μm. The ceramic powder layer 23 is generally about 0.5 mm to about 50 mm thick.

The glass envelope 24 may be formed of silica glass, boron oxide glass, silicate glass, borosilicate glass, germanate glass, phosphate glass or the like. It is generally about 100 μm to about 5,000 μm thick.

These elements are assembled as follows. First, a suitable support material is shaped and finished to form a substrate or support 11 of predetermined configuration and dimensions depending on the intended use. Separately a ceramic material is sintered to form a hollow cylindrical cover or sleeve 12. The cover or sleeve 12 generally has a wall thickness of up to 10 mm, preferably 10 μm to 3 mm. Then the substrate 11 is fitted and received in the cover 12 as shown in FIG. 1. Preferably the substrate 11 is snugly fitted in the cover 12 with the gap therebetween being as small as 0.3 mm or less.

The substrate 11 has substantially the same configuration as the final product. More particularly, the substrate 11 may be provided with grooves, recesses, ridges, or rims on its surface if desired. In the illustrated example, the substrate 11 is a cylinder formed with a circumferential groove at an axial intermediate. The configured substrate 11 may be prepared by sintering, casting, and/or machining.

Also, the cover 12 has substantially the same outer configuration as the final product. However, the cover 12 may take a simple configuration having a smooth outer surface while necessary surface irregularities can be omitted at this point. This leads to efficient manufacture because only the substrate 11 need precise shaping and the cover 12 can have a simple configuration. The simple configuration allows the cover to be formed to a uniform wall thickness, resulting in the final coating with a uniform thickness.

Instead of prefabricating a cover of a sintered ceramic material, it is also contemplated herein to apply a sintered ceramic material to a substrate and subject the coated substrate to superplastic forming. The sintered ceramic material can be applied to the substrate by any well-known coating methods including spray coating, welding, solution coating, and sputtering.

The spray coating often relies on a plasma or gas and uses a coating material having a particle size of #50 to #500. A material with a particle size of less than #50 does not smoothly flow during spray coating whereas particles of larger than #500 are difficult to deposit.

The welding method is by mixing together the ceramic material and glass both serving as coating materials in the presence of water to form a paste, coating and sintering the paste to the substrate. The sintering temperature is higher than the softening temperature of glass, usually 400° to 1,000° C. The glass used may be selected from silica, borate, silicate, borosilicate and phosphate glasses, with the borosilicate glass being preferred because of appropriate welding temperature. The amount of glass blended is 5 to 80% by weight, preferably 15 to 60% by weight based on the total weight of the coating material. With less than 5% by weight of glass, the coating material would not firmly adhere to the substrate. More than 80% by weight of glass adversely affects biological affinity.

In the case of solution coating, the coating material is dissolved to saturation in a medium such as hydrochloric acid, sulfuric acid, and nitric acid. The solution is applied to the substrate by coating or dipping and then heated to a temperature of at least 300° C. in an inert gas. Heating temperatures of lower than 300° C. are too low to provide a bond whereas temperatures of higher than 1,000° C. would deteriorate certain substrate materials, imposing limitation on the substrate material.

Sputtering is carried out by mounting a target of coating material in a sputtering device, effecting pre-sputtering for a certain time, usually for 5 to 60 minutes, then heating the substrate to a temperature of about 20° to 500° C., and effecting substantial sputtering. The sputtering times depends on the desired film thickness. After sputtering, the coated substrate is often post treated at 100° to 1,300° C.

Next, the assembly of substrate 11 fitted in cover 12 in the former embodiment or the coated substrate 11 in the latter embodiment is covered with ceramic powder 23 and enclosed in the glass envelope 24 as shown in FIG. 2.

The envelope is then loaded in a conventional HIP apparatus which applies heat and pressure to the envelope, creating a strong junction between substrate 11 and cover 12. There results an integral or composite body 1 in which a coat 15 is closely bonded to the substrate 11 as shown in FIG. 3. At the end of HIP forming, the glass envelope 24 is broken and the integral body 1 is taken out.

During the HIP process, the substrate 11 is little deformed and the coat 15 of uniform thickness closely conforms to the outer contour of substrate 11. The isostatic pressing minimizes the chance of poor bond.

The coat 15 on the formed composite body 1 generally has a thickness of from about 1 $\mu$m to about 10 mm, preferably from 1 $\mu$m to 5 mm, more preferably from 10 $\mu$m to 3 mm. The coat 15 does not peel away even when it is relatively thick as several millimeters.

The coat 15 can be finished to a mirror or rough surface through a proper choice of the particle size of the surrounding ceramic powder 23. For increased surface area and biological activity, the coat should have a rough surface having a surface roughness Rmax of about 10 to about 500 $\mu$m.

The superplastic junction using an HIP process has been described. In the practice of the invention, a hot pressing (HP) process may also be used to establish a junction insofar as the substrate 11 having substantially the same configuration as the final composite body 1 can be combined with a cover 12 of a simple configuration capable of fitting over the substrate.

The HP process involves the steps of engaging the substrate 11 with the cover 12 in place, embedding the assembly in the ceramic powder 23 in a press mold, and forcing a punch thereto. The press mold is preferably formed of the same or similar material as the ceramic powder. Then a bond is established to a degree substantially equal to the HIP process.

The superplastic forming of a sintered ceramic material, which may be either a calcium oxide and silicon oxide-containing, non-calcium phosphate ceramic material in the first form or a calcium phosphate ceramic matrix/inorganic filler composite material in the second form, results in a single body or a integrated body depending on whether or not the ceramic material is combined with a substrate, both the single and integrated bodies serving as living hard tissue replacements.

The living hard tissue replacements may be utilized as parts at least partially embedded in a living body, for example, artificial dental parts such as dental roots and crowns, artificial bones (including general bones, skull, ossiculum auditus, jaw bone, cartilagines ansi, etc.), bone replacements, artificial joints, fracture fixtures, artificial valves, and artificial blood vessels as well as medical equipment, for example, hypodermic implanting equipment such as dialysis shunts, living body embedding equipment such as pacemakers, and other living body indwelling equipment.

Now, the application of the integrally formed body of the invention to an artificial dental root and crown as a typical living hard tissue replacement is described. The artificial dental root and crown are preferably of the construction in which a sintered ceramic material is joined to the surface of a substrate by superplastic forming.

Figure 4:
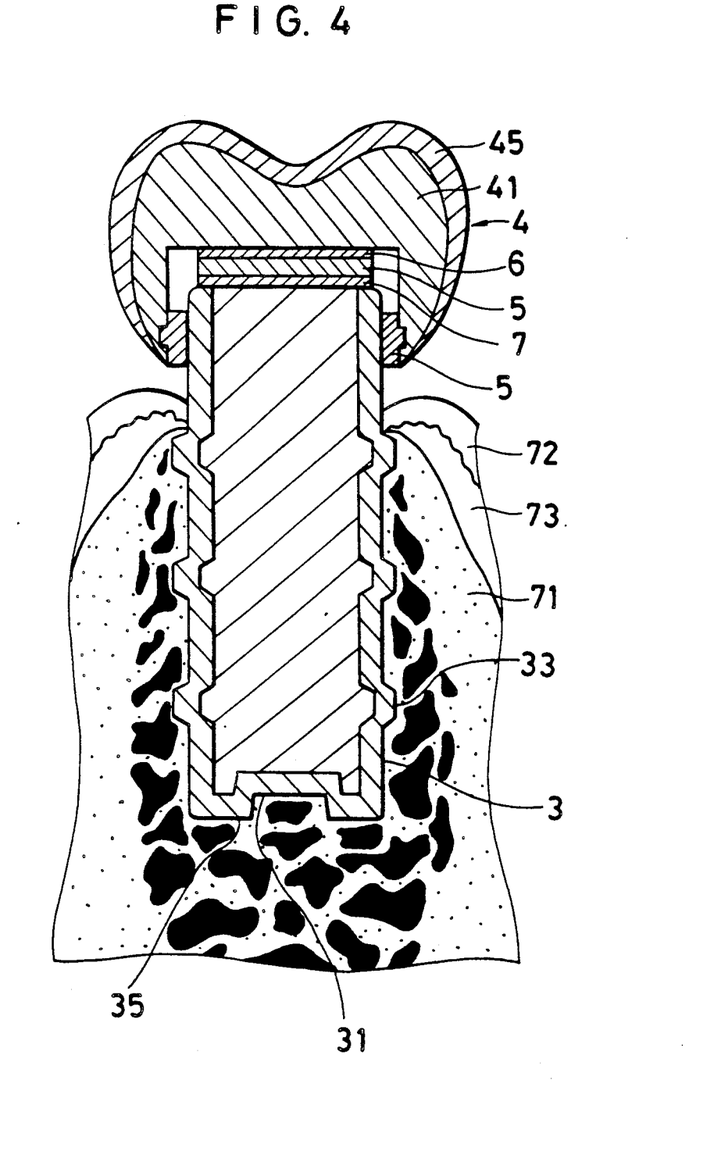
FIG. 4 is a cross-sectional view of a dental root implanted in an alveolar bone, the root having a crown cemented thereto.

FIG. 4 shows an artificial dental root and crown according to one preferred embodiment of the invention. An artificial dental root 3 to which a crown 4 is secured through a damping member 5 by cement layers 6 and 7 is implanted in an alveolar bone 71.

The dental root 3 includes a root substrate 31 and a coat layer 35 bonded to the substrate surface. The root 3 on the outer surface is formed with a plurality of tabs or threads 33. The tabs 33 have an anchoring function and a function of defining gaps between the root 3 and the alveolar bone 71. The root 3 does not directly integrate with the surrounding alveolar bone 71, but a neoblastic bone which will form around the root. The provision of tabs 33 promotes the growth of a new bone, ensuring a firm bond between the root 3 and the alveolar bone 71. The shape of tabs 33 is not critical, and they may be circumferential rings, screw threads or discrete protuberances on the outer surface of the root 3. The tabs 33 are generally 100 μm to 3 mm in radial height.

The configuration and dimensions of substrate 31 are not critical. The substrate may be configured to the shape and dimensions corresponding to the intended artificial dental root as previously described. It is preferably formed with tabs corresponding to the tabs 33. It is preferably formed from a safe material having high mechanical strength and toughness as previously described, inter alia, titanium, titanium alloy, zirconia, and monocrystalline alumina (sapphire).

The coat layer 35 on the root substrate 31 is formed from a sintered ceramic material and joined to the substrate 31 by superplastic forming. The coat layer 35 is initially a hollow cylinder having one closed end and one open end formed from a sintered ceramic material and adapted to fit over the substrate 31. The cover cylinder is preferably about 10 μm to about 10 mm thick. The superplastic forming causes the cover cylinder of ceramic material to deform in conformity with the outer contour of substrate 11 and to bond to the substrate 11 without leaving a gap. The coat layer 35 of uniform thickness is joined to the substrate 11 in this way. The coat layer 35 preferably has a thickness of 1 μm to 5 mm, more preferably from 10 μm to 2 mm.

The coat layer 35 should be present at least on those surface areas of the artificial dental root 3 which come in contact with a living body, for example, the alveolar bone 71, gingival epithelium 72, and subepithelial connective tissue 73 in FIG. 4.

The artificial dental root 3 of the above-mentioned construction is not particularly limited in shape. A choice may be made of circular, oval, and rectangular column and blade shapes. It is preferred to provide tabs 33 as previously described. In general, the artificial dental root 3 has a maximum diameter of 2 to 20 mm and a height of 3 to 50 mm. It may be configured to any desired dimensions in accordance with various standards or to special dimensions if necessary.

Although the artificial dental root 3 shown in FIG. 4 is a one-piece member, the invention is also applicable to two-piece dental roots having a post core and multiple-piece dental roots having three or more components. These roots should have a coat layer of ceramic material on at least the surface to be in contact with a living body.

The dental crown 4 includes a coronal substrate 41 and a coat layer 45 bonded to the substrate surface. The coat layer 45 is formed of sintered ceramic material and joined to the coronal substrate 41 by superplastic forming. An initial cover which is fitted over the substrate and eventually converted into the coat layer 45 may have any appropriate thickness depending on the desired configuration and thickness of the coat layer.

The configuration and dimensions of coronal substrate 41 are not critical. The coronal substrate 41 may be configured to a columnar or pyramid shape having a recess at its bottom for receiving the root or a combination of such shapes. The top side of the coronal substrate 41 may be flat, but preferably configured to a complex shape conforming to the intended crown. More particularly, the crown configuration largely differs between incisive and molar teeth. Thus, the use of a coronal substrate 41 configured to a shape conforming to a particular incisive or molar tooth leads to ease of forming because the sintered ceramic material requires minimal deformation. The material of which the coronal substrate 41 is formed may be selected from the same materials as previously mentioned for the root substrate.

In order that the crown 4 have an aesthetic appearance similar to a natural tooth, biological affinity, and no detrimental influence to the gingival epithelium 72, the coat layer 45 should preferably surround the entire outer surface of the coronal substrate 41. The coat layer 45 generally has a thickness of about 1 μm to about 5 mm.

The crown 4 illustrated in FIG. 4 is a single component crown although the present structure is applicable to the outer crown component of a two-component crown.

The artificial dental crown 4 is secured to the artificial dental root 3 through the damping members 5 by cement layers 6 and 7 as shown in FIG. 4. The damping members 5 are effective for damping shocks applied to the root during mastication and gnash. Cementing of the crown to the root through the damping members allows the crown to fluctuate like a natural tooth. The damping members 5 are often formed of synthetic rubber to a thickness of about 0.01 to about 4 mm. The cement layers 6 and 7 may be of a conventional dental cement.

The artificial dental root according to the invention is not only useful as an implant embedded in an alveolar bone when combined with the artificial crown as shown in FIG. 4, but also as an intradental implant by inserting the artificial root into a natural tooth.

The artificial dental root combined with the artificial dental crown according to the invention is also useful in full and partial denture sets, and free-standing tooth replacements.

The artificial dental root and crown according to the invention may be independently used in practice. That is, the artificial dental crown and root to be combined with the artificial dental root and crown according to the invention, respectively, need not have a coat layer of sintered ceramic material. The artificial dental root and crown according to the invention are effective even when they are combined with conventional artificial dental crown and root.

EXAMPLE

Examples of the present invention are given below by way of illustration and not by way of limitation.

EXAMPLE 1

Diopside having an average particle size of 1.0 μm was subjected to unidirectional pressing under a pressure of 300 kg/cm$^2$, and then to cold isostatic pressing (CIP) under a pressure of 2,000 kg/cm$^2$. It was then calcined for two hours at 1,000° C. in air and then HIP sintered for two hours at 1,150° C. and 2,000 kg/cm$^2$ in argon gas, obtaining a cylindrical sintered body. This cylindrical sintered body had a diameter of 4 mm, a height of 8 mm, a relative density of 99.9%, and an average grain size of 1.1 μm.

The relative density was determined by measuring the density of a sintered sample by the Archimedian method. The sintered sample was pulverized into powder having a surface area of 5 m²/g which was measured for true density. Relative density was calculated from the apparent and true densities.

The average grain size was determined by means of a scanning electron microscope by determining an average grain area and determining the average diameter of a phantom circle having the average grain area.

The sintered body had a flexural strength of 300 MPa and a fracture toughness of 3.5 MPam$\frac{1}{2}$. It is to be noted that flexural strength was determined by cutting out ten test specimens of 3×4×40 mm, mirror polishing them, and measuring by the three point bending test with a span of 36 mm and a cross head speed of 0.5 mm/min. Fracture toughness (KiC) was measured according to ASTM E399-83.

The sintered body was subjected to forming in an inert gas atmosphere using an artificial dental root-shaped mold of molybdenum base alloy (TZM). The forming conditions included a holding temperature of 1,050° C., a compression rate of 1.0 mm/min., a compression force of 50 MPa, and a deformation of 0.5 in true strain. The forming resulted in an artificial dental root of diopside. It was observed at the end of forming that the average grain size was 1.0 μm and the grains had been distorted and oriented.

EXAMPLE 2

Diopside was subjected to unidirectional pressing under a pressure of 300 kg/cm², and then to cold isostatic pressing (CIP) under a pressure of 2,000 kg/cm². It was then calcined for two hours at 1,000° C. in air and then HIP sintered for two hours at 1,150° C. and 200 MPa in argon gas, obtaining a hollow cylindrical sintered body. It had a wall thickness of 1 mm, an inner diameter of 5.1 mm, and a height of 8 mm. It had an average grain size of 1.2 μm, a coefficient of thermal expansion of $12\times10^{-6}$, a flexural strength of 300 MPa, and a fracture toughness (KiC) of 3.5 MPam$\frac{1}{2}$.

A solid columnar piece of titanium (having a coefficient of thermal expansion of $8.4\times10^{-12}$) serving as a root substrate was fitted in the hollow sintered cylinder as shown in FIG. 1. The titanium piece had a diameter of 5 mm, a height of 10 mm and a circumferential recess of 1 mm deep on the outer surface (see FIG. 1). The assembly was covered with BN ceramic powder having a high melting point (which does not melt at 700° C. or higher) and an average particle size of 15 μm, and further enclosed in a silica glass envelope as shown in FIG. 2. Superplastic forming was effected by an HIP process under the conditions: a temperature of 1,100° C., a pressure of 30 MPa, and a time of 30 minutes.

At the end of HIP forming, the glass envelope was broken and the BN powder was brushed off. There was obtained an artificial dental root having a diopside coat layer of 1 mm thick joined to the root substrate surface. The bond strength between the substrate and the coat layer was 100 MPa, as represented by the peel strength which was measured by withdrawing the root substrate from the joined root substrate-coat assembly secured in a jig. The coat layer had a surface roughness Rmax of 12 μm. The entire root had as high flexural strength and fracture toughness (KiC) as the Ti substrate.

A biological affinity test was performed on the dental root sample of this Example.

The dental roots were implanted in holes of 3×4×6 mm formed in the jaw bone of male adult rabbits weighing 2.5 to 2.8 kg. Polished, but non-decalsified specimens were prepared after the lapse of six weeks from the operation. An SEM photomicrograph was taken on the interface between the root and the newly grown bone. It was found that a biologically active interfacial film formed between the diopside implant and the bone and that the newly grown bone completely adhered to the root (implant) and penetrated and filled into pores therein, proving that the root had high biological affinity.

A high resolution image was taken under a TEM on the interface between the artificial dental root and the matrix bone after 24 weeks. The sequence of bone cells was identical on both the root and matrix bone sides, with little or no distinct boundary observed therebetween.

For comparison purposes, a junction was created by superplastic forming according to the same procedure as above except that the cover material was changed from diopside to hydroxyapatite (HAP) and the HIP superplastic forming temperature was 1,000° C. Although the HAP coat could be joined to the Ti substrate, the HAP coat which was less stress resistant was broken by the application of repetitive stresses.

EXAMPLE 3

The same substrate-coat assembly as in Example 2 was placed in a mold of SiC ceramic. The space between the assembly and the mold was charged with SiC ceramic powder having an average particle size of 15 μm. Superplastic forming was effected by a hot pressing (HP) process. The HP conditions included a temperature of 1,100° C., a pressure of 20 MPa, and a time of 20 minutes.

At the end of HP forming, the assembly, that is, artificial dental root was taken out of the SiC ceramic mold. The dental root of this example was equivalent to that of Example 2 with respect to bond strength, flexural strength and biological affinity.

EXAMPLE 4

Stock materials of CaO, SiO₂, and MgO were mixed to provide compositions corresponding to the diopside, akermanite, wollastonite, alite, or belite fields as shown in Table 1. With a binder added, the compositions were press molded and then sintered at 1,200° to 1,360° C. for two hours. The sintered ceramic materials had a grain size in the range of from 0.7 to 1.5 μm and a relative density of 99.5% or higher. Table 1 also reports the content (in % by volume) of the ceramic composition in the sintered body as measured by an X-ray powder diffraction method.

The sintered materials were subjected to HIP superplastic forming at a forming temperature of 1,100° to 1,170° C. as described in Example 2.

The resulting articles showed satisfactory bond strength, flexural strength and biological affinity and were thus suitable as dental roots.

TABLE 1

| Cover composition (wt %) | | | | Cover sintering temp. | Grain size | Ceramic composition*/ content | Density | Flexural strength | KiC | Forming temp. |
|---|---|---|---|---|---|---|---|---|---|---|
| CaO | SiO$_2$ | MgO | Field* | (°C.) | (μm) | (vol %) | (%) | (MPa) | (MPam$^{\frac{1}{2}}$) | (°C.) |
| 23.3 | 62.5 | 14.2 | D | 1200 | 1 | D/55 | 99.8 | 290 | 3.6 | 1100 |
| 24.6 | 55.2 | 20.2 | D | 1230 | 1 | D/65 | 99.9 | 270 | 3.3 | 1100 |
| 25.9 | 55.5 | 18.6 | D | 1220 | 1.5 | D/60 | 99.6 | 300 | 3.4 | 1100 |
| 41.1 | 44.1 | 14.8 | A | 1250 | 0.7 | A/50 | 99.7 | 250 | 2.2 | 1120 |
| 48.3 | 51.7 | | W | 1350 | 1 | W/60 | 99.5 | 300 | 2.5 | 1150 |
| 73.7 | 26.3 | | AL | 1360 | 1.5 | AL/55 | 99.8 | 230 | 2.2 | 1170 |
| 65.1 | 34.9 | | B | 1350 | 1 | B/55 | 99.5 | 220 | 2.2 | 1150 |

*D: diopside
A: akeramanite
W: wollastonite
AL: alite
B: belite

EXAMPLE 5

A cylindrical substrate of titanium having a diameter of 5 mm and a height of 10 mm was blasted with 100-mesh steel shots. Titanium particles of 150 to 250 mesh were applied to the blasted surface of the titanium substrate by plasma spraying at a voltage of 60 V and a current of 500 A in an atmosphere of argon/hydrogen (5:1).

The substrate was further coated with a dispersion of diopside powder of 60 to 100 mesh in water and dried. The diopside coated substrate was covered with BN ceramic powder, enclosed in a silica glass envelope, and subjected to superplastic forming by an HIP process. The HIP forming conditions included a temperature of 1,000° C., a pressure of 20 MPa, and a time of 30 minutes.

At the end of HIP forming, the glass envelope was broken and the BN powder was brushed off. There was obtained an artificial dental root having a diopside coat layer joined to the root substrate. The dental root of this example was equivalent to those of Examples 2 to 4 with respect to bond strength, flexural strength and biological affinity.

EXAMPLE 6

As reported in Table 2, hydroxyapatite (HAP) and whisker-forming material were milled along with a dispersant in a ball mill for one hour. The slurry was filtered through a qualitative filter paper. The collected cake was dried at 120° C. for 5 hours and a 50-gram portion of the cake was then molded in a mold of 40 mm by 50 mm under a pressure of 300 kg/cm$^2$. The molded material was sintered at the temperature shown in Table 2 for 2 hours, obtaining a sintered body useful as biomedical material.

The hydroxyapatites used had an atomic calcium-to-phosphorus (Ca/P) ratio of 1.67 and the BET values shown in Table 2.

The whisker-forming materials used were anorthites and diopsides having the BET values shown in Table 2. The amount of whisker-forming material added is reported in Table 2 in % by weight based on the total weight of HAP plus whisker-forming material. The whisker-forming materials used are as identified below.

Anorthite A: sintered CaO.Al$_2$O$_3$.2SiO$_2$.
Anorthite B: a mixture of SiO$_2$ 61% by weight, Al$_2$O$_3$ 17% by weight, and CaO 22% by weight.
Anorthite C: a mixture of SiO$_2$ 50% by weight, Al$_2$O$_3$ 30% by weight, and CaO 20% by weight.
Diopside A: sintered CaO.MgO.2SiO$_2$.
Diopside B: a mixture of SiO$_2$ 61% by weight, MgO 12% by weight, and CaO 27% by weight.
Diopside C: a mixture of SiO$_2$ 55% by weight, MgO 19% by weight, and CaO 26% by weight.

The BET values of anorthites B and C and diopsides B and C are those of mixtures of respective ingredients.

The dispersant was SN Dispersant 5045 manufactured and sold by SAN NOPCO Limited and was used in an amount of 0.05% by weight based on the total weight of HAP plus whisker-forming material.

The thus obtained biomedical materials were sectioned and observed under an electron microscope to determine their whisker amount, matrix grain size (D), whisker length (L), whisker aspect ratio, and matrix grain size/whisker length ratio (D/L). They were also measured for relative density, flexural strength (F.S.), and fracture toughness (KiC). The results are shown in Table 3.

Photomicrographs of sample Nos. 1 to 10 taken under a scanning electron microscope (SEM) showed that each sintered body had a structure in which anorthite or diopside whiskers were dispersed among hydroxyapatite grains.

The samples were observed under an analytical electron microscope (ATEM). The profiles of Si, P and Ca contents were determined from X-ray peaks of Si, P and Ca to find the presence of a vitreous phase containing Ca, P and Si along the grain boundaries, indicating a graded concentration of the respective elements.

Figure 5:
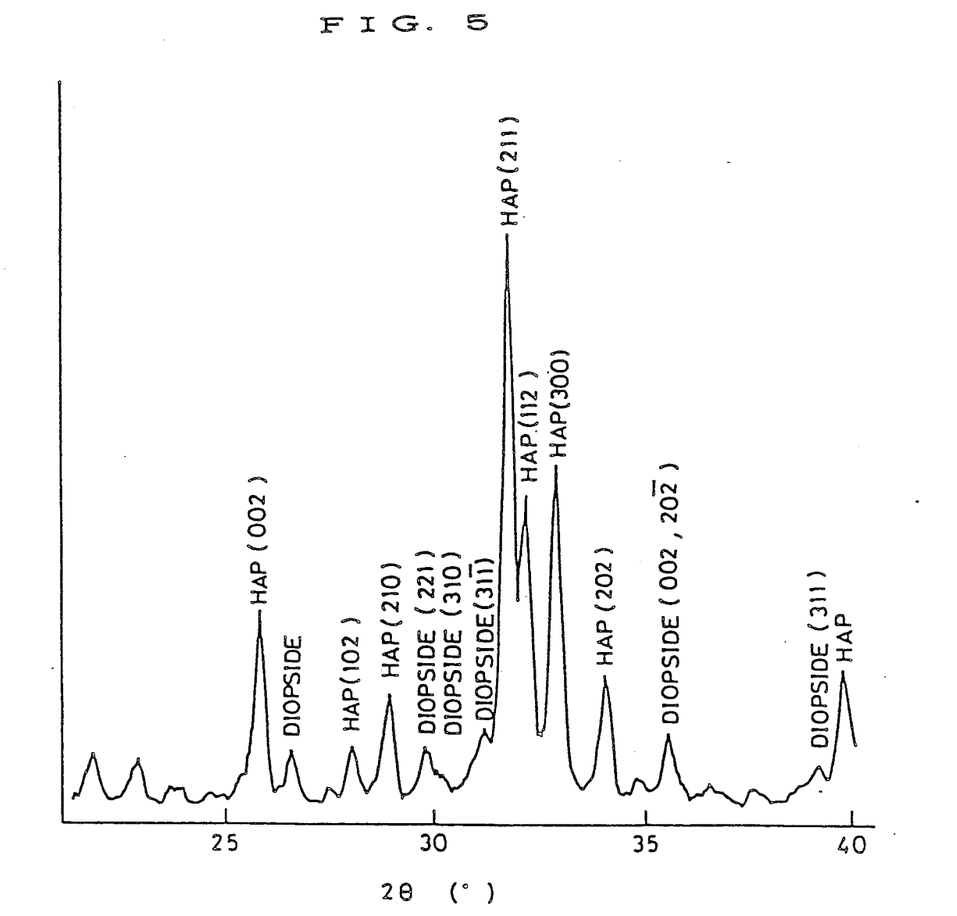
FIGS. 5 and 6 are diagrams of X-ray diffraction analysis of sample Nos. 2 and 3 in Example 6, composite sintered materials containing inorganic fillers in a ceramic matrix, respectively.
Figure 6:
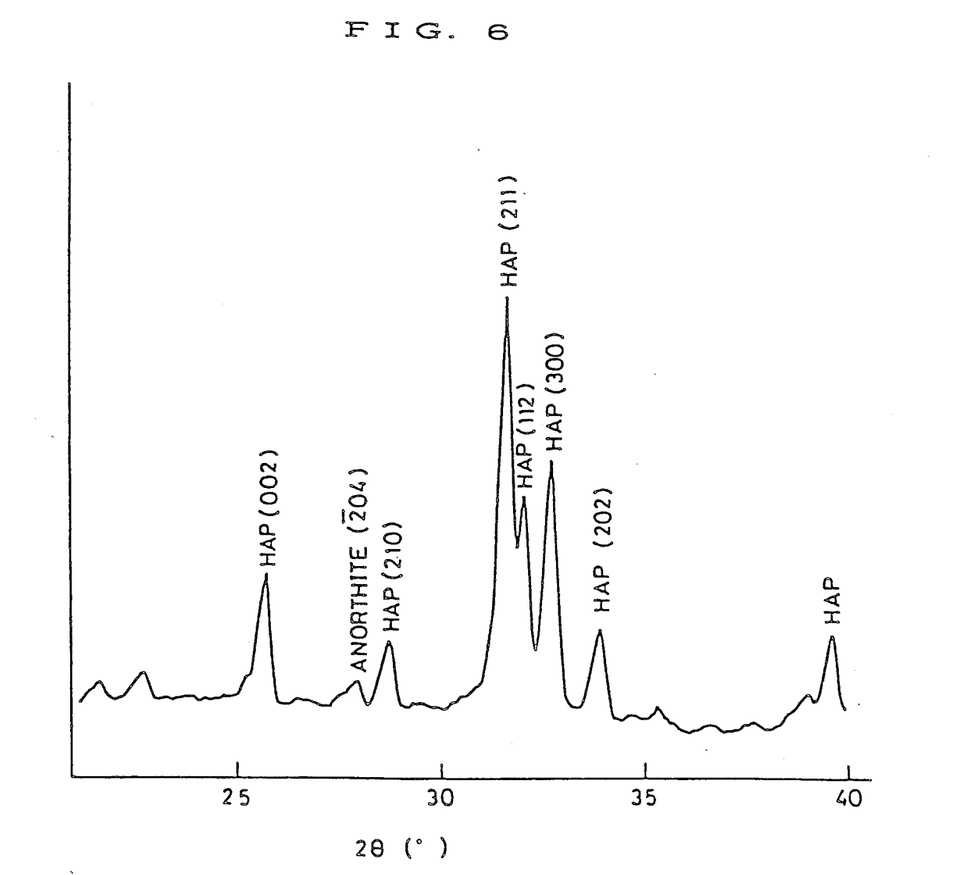

FIGS. 5 and 6 are X-ray diffraction diagrams of sample Nos. 2 and 3, indicating that anorthite or diopside whiskers are formed in hydroxyapatite.

TABLE 2

| | HAP* | Whisker-forming material | | | Sintering |
|---|---|---|---|---|---|
| Sample No. | BET (m$^2$/g) | Type | Amount (wt %) | BET (m$^2$/g) | temp. (°C.) |
| 1 | 80 | anorthite A | 20 | 5 | 1220 |
| 2 | 20 | diopside A | 20 | 10 | 1250 |
| 3 | 80 | anorthite B | 20 | 8 | 1250 |
| 4 | 15 | diopside B | 20 | 10 | 1270 |
| 5 | 80 | anorthite C | 20 | 15 | 1180 |
| 6 | 20 | diopside C | 20 | 15 | 1220 |
| 7 | 80 | anorthite A | 20 | 30 | 1160 |
| 8 | 30 | diopside A | 20 | 30 | 1200 |
| 9 | 80 | diopside A | 40 | 30 | 1220 |
| 10 | 80 | diopside A | 60 | 30 | 1240 |

*HAP: Ca/P = 1.67

TABLE 3

| Sample No. | Whisker content (area %) | Matrix grain size D (μm) | Whisker length L (μm) | Whisker aspect ratio | D/L | Relative density (%) | Flexural strength (MPa) | $K_1C$ (MPa√m) |
| --- | --- | --- | --- | --- | --- | --- | --- | --- |
| 1 | 10 | 4 | 6 | 7 | 0.67 | 99.5 | 140 | 1.3 |
| 2 | 10 | 4 | 13 | 11 | 0.3 | 99.5 | 160 | 1.4 |
| 3 | 15 | 3 | 13 | 13 | 0.23 | 99.5 | 190 | 1.9 |
| 4 | 15 | 5 | 14 | 15 | 0.35 | 99.5 | 180 | 1.9 |
| 5 | 17 | 0.3 | 0.5 | 8 | 0.6 | 99.0 | 200 | 1.8 |
| 6 | 17 | 5 | 4 | 3 | 1.25 | 99.5 | 220 | 1.8 |
| 7 | 18 | 0.3 | 0.3 | 11 | 1.0 | 99.5 | 220 | 2.5 |
| 8 | 18 | 1 | 2 | 10 | 0.5 | 99.8 | 230 | 2.8 |
| 9 | 35 | 0.5 | 2 | 15 | 0.25 | 99.9 | 290 | 3.3 |
| 10 | 45 | 0.7 | 2 | 15 | 0.35 | 99.5 | 320 | 3.6 |

Sample Nos. 1 to 10 were examined for biological activity. The samples were immersed in pseudo body fluid for a predetermined time and examined by an SEM observation and chemical analysis as to whether or not an HAP layer precipitated on the surface.

It was found that an HAP layer precipitated on the surface after 3 days for diopside whiskers and after 10 days for anorthite whiskers, proving that all the samples were biologically active.

It is generally believed that in order that an implant adhere and bond to a living bone in vivo, it is essential that a HAP layer similar to the natural bone forms on the surface of the implant. The sintered composite bodies of the invention are biologically highly active in this respect.

Next, artificial dental roots of integrated structure were fabricated.

Covers were prepared by molding the sintered composite bodies into a hollow cylindrical shape having a wall thickness of 1 mm, an inner diameter of 5.1 mm and a height of 8 mm.

A solid columnar piece of titanium serving as a root substrate was fitted in the sintered cover. The titanium piece had a diameter of 5 mm, a height of 10 mm and a circumferential recess of 1 mm deep on the outer surface. The assembly was subjected to HIP superplastic forming under the same conditions as in Example 1.

The resulting dental roots showed excellent properties equivalent to those of Examples 2 to 5.

EXAMPLE 7

Artificial dental crowns were fabricated. Hollow cylindrical sintered covers were prepared as in Examples 2, 4, and 5. The covers were fitted over coronal substrates of titanium. The assembly was subjected to HIP superplastic forming under the same conditions as used for the dental roots. The resulting dental crowns showed excellent properties equivalent to those of the dental roots.

There has been described a living hard tissue replacement or implant fabricated by the superplastic forming of a ceramic material containing CaO and SiO$_2$. The superplastic forming ensures ease of shaping to a complex profile, eliminating a need for profile finishing by machining. There is no chance that flaws which would induce cracks during repetitive use be introduced into the replacement. The outer surface of the replacement as formed has a desirable irregular complex profile which cannot be reproduced by machining.

The ceramic material, typically diopside can be joined to a heterogeneous material by an HIP process. There is obtained a living hard tissue replacement having a diopside layer firmly bonded to a substrate of heterogeneous material. A joint can be established at relatively low temperatures.

The method for superplastic joining a ceramic coating to a substrate often uses hot isostatic pressing (HIP) for taking its advantage of even application of pressure to the object and thus produces an integrated article which leaves no gaps at the substrate-coating interface, exhibits an increased bonding force, and experiences no or little interfacial delamination during repetitive use.

Since no exfoliation occurs with an increasing thickness of a coat layer of sintered ceramic material or sintered composite material, the coat layer can have any desired thickness. The coat layer may be either as thin as about 1 μm or as thick as about 10 mm. The coat layer thickness may be selected over the wide range depending on the intended use. In addition, the coat layer can be applied to a uniform thickness without a substantial variation and to a complex configuration with ease. The variation in quality among products is minimized.

The replacements can be controlled to any desired surface roughness through a choice of the particle size of ceramic powder to be filled around the ceramic material or coating/substrate assembly during HIP or HP forming.

An integrated body can be prepared from a substrate and a cover by shaping only the substrate to a precise configuration, fitting the ceramic cover of a roughly conforming shape over the substrate, and subjecting the assembly to superplastic forming. Steps of shaping, bonding, and surface treatment can be concurrently performed by a single forming step, with the benefits of eliminated need for machining and increased efficiency of working and manufacture. A plurality of integrated bodies can be produced at the same time so that a cost reduction is expectable from potential mass production.

It is also possible to apply an HIP or HP process to a substrate coated with a superplastic ceramic material in powder form. This embodiment achieves a further cost reduction by omitting a step of pre-forming a cover by sintering.

The living hard tissue replacements of the invention have extremely high mechanical strength and toughness as compared with those composed solely of calcium phosphate base ceramic materials.

In summary, the present invention enables economical production of living hard tissue replacements featuring improved mechanical strength, biological affinity, and formability and well suited as artificial dental roots and crowns.

Although some preferred embodiments have been described, many modifications and variations may be made thereto in the light of the above teachings. It is therefore to be understood that within the scope of the appended claims, the invention may be practiced otherwise than as specifically described.

We claim:

1. A living hard tissue replacement prepared by the superplastic forming of a ceramic material having crystalline grains which contains CaO and $SiO_2$ as essential components, is substantially free from calcium phosphate, but capable of forming a calcium phosphate base compound upon contact with a phosphorus-containing aqueous solution.

2. The living hard tissue replacement of claim 1 wherein said ceramic material further contains MgO in addition of the essential components CaO and $SiO_2$.

3. The living hard tissue replacement of claim 2 wherein said ceramic material contains 10 to 90% by weight of CaO, 10 to 80% by weight of $SiO_2$, and 0 to 35% by weight of MgO.

4. The living hard tissue replacement of claim 3 wherein said ceramic material has a composition selected from the group consisting of diopside, wollastonite, akermanite, monticellite, alite, and belite.

5. The living hard tissue replacement of claim 4 wherein said ceramic material contains at least 40% by volume of a diopside or wollastonite composition.

6. The living hard tissue replacement of claim 1 in the form of an artificial dental root or crown.

7. A method for preparing a living hard tissue replacement comprising the step of superplastic forming a ceramic material having crystalline grains which contains CaO and $SiO_2$ as essential components, is substantially free from calcium phosphate, but capable of forming a calcium phosphate base compound upon contact with a phosphorus-containing aqueous solution.

8. The method of claim 7 wherein said ceramic material further contains MgO in addition of the essential components CaO and $SiO_2$.

9. The method of claim 8 wherein said ceramic material contains 10 to 90% by weight of CaO, 10 to 80% by weight of $SiO_2$, and 0 to 35% by weight of MgO.

10. The method of claim 9 wherein said ceramic material has a composition selected from the group consisting of diopside, wollastonite, akermanite, monticellite, alite, and belite.

11. The method of claim 10 wherein said ceramic material contains at least 40% by volume of a diopside or wollastonite composition.

* * * * *